United States Patent
Militzer

[11] Patent Number: 6,036,147
[45] Date of Patent: Mar. 14, 2000

[54] PORTABLE SECTIONAL POLE AND ATTACHING CONNECTORS

[76] Inventor: George G. Militzer, 1402 Carleton Sq., San Diego, Calif. 92106

[21] Appl. No.: 09/012,847

[22] Filed: Jan. 23, 1998

[51] Int. Cl.[7] ................................................. F16M 13/00
[52] U.S. Cl. .................... 248/159; 248/125.8; 248/230.8
[58] Field of Search ................................ 248/159, 125.1, 248/125.3, 125.8, 230.8, 228.8, 218.4, 230.1; 211/86.01, 171, 172, 173

[56] References Cited

U.S. PATENT DOCUMENTS

| | | | |
|---|---|---|---|
| 3,526,056 | 9/1970 | Stropkay | 47/42 |
| 3,698,564 | 10/1972 | Muller | 211/86 |
| 3,709,556 | 1/1973 | Allard et al. | 297/188 |
| 3,908,943 | 9/1975 | Bannister | 248/159 |
| 4,332,378 | 6/1982 | Pryor | 248/125 X |
| 4,461,387 | 7/1984 | Belokin, Jr. | 248/159 X |
| 4,511,157 | 4/1985 | Wilt | 280/289 |
| 4,541,596 | 9/1985 | Price | 248/125 |
| 4,744,536 | 5/1988 | Bancalari | 248/125 |
| 4,767,131 | 8/1988 | Springer et al. | 248/316.2 X |
| 5,009,442 | 4/1991 | Schneider | 280/304.1 |
| 5,135,191 | 8/1992 | Schmuhl | 248/125 |
| 5,188,323 | 2/1993 | David | 248/158 |
| 5,222,946 | 6/1993 | Kamen | 604/151 |
| 5,337,992 | 8/1994 | Pryor | 248/125 |
| 5,366,191 | 11/1994 | Bekanich | 248/125 |
| 5,374,074 | 12/1994 | Smith | 280/304.1 |
| 5,494,248 | 2/1996 | Pratt et al. | 248/311.2 |
| 5,632,461 | 5/1997 | Von Helms et al. | 248/230.8 X |
| 5,704,577 | 1/1998 | Gordon | 248/125 X |

*Primary Examiner*—Derek J. Berger
*Assistant Examiner*—Tan Le
*Attorney, Agent, or Firm*—Frank G. Morkunas

[57] ABSTRACT

A pole connector and a detachable sectional pole wherein the pole connector, at one end, is securely insertable into one end of a section of the pole, while another end of the connector defines a set of at least three fins protruding from that pole section for removably attaching to a mouth of another pole section. The pole connector may be made of two to four or more segments. The sectional pole has more than one section, each with a pole connector securably inserted into one end with the other end being a mouth adapted to removably connect to a pole connector protruding from another pole section. The sectional pole has a support member adapted to attach to an external object, maintain approximate vertical stability, and protect the external object from damage while so attached. The sectional pole also has one or more holding members which are either concealable within the sectional pole or removable from the sectional pole and which are adapted to hold external objects thereon.

16 Claims, 5 Drawing Sheets

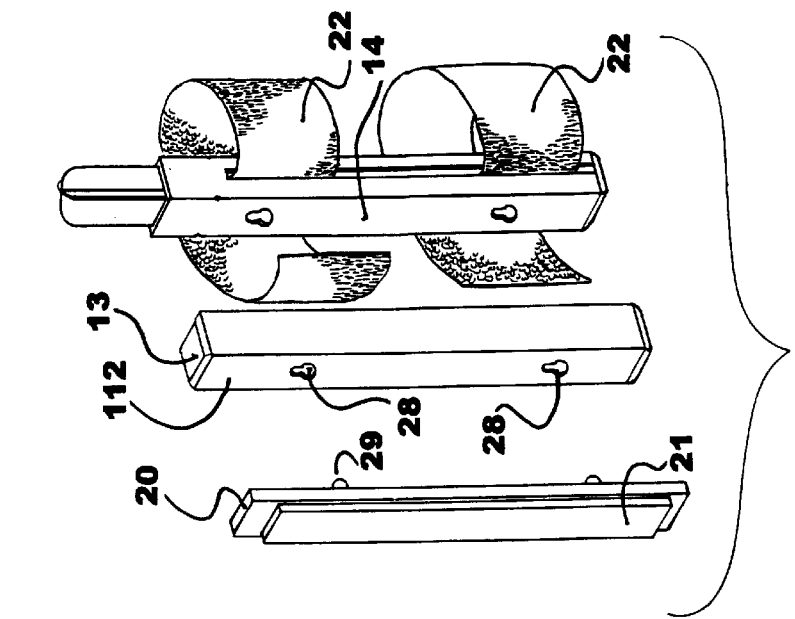
FIGURE 7
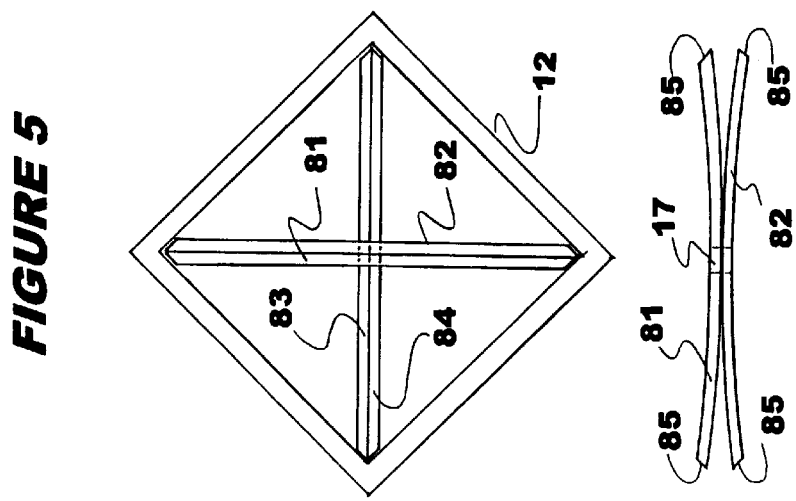
FIGURE 5
FIGURE 6
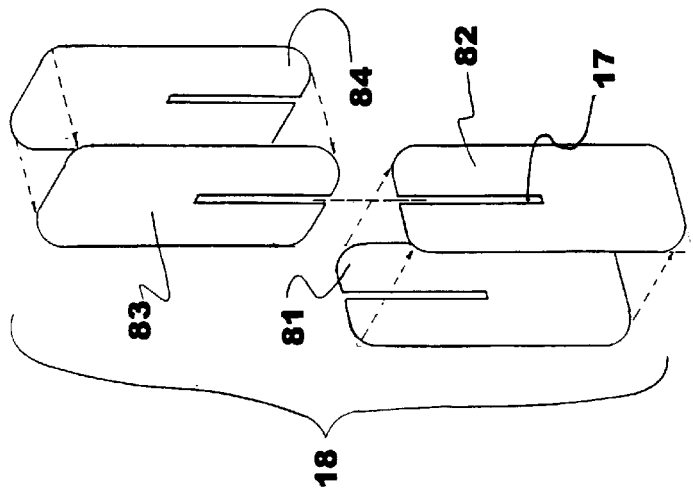
FIGURE 4

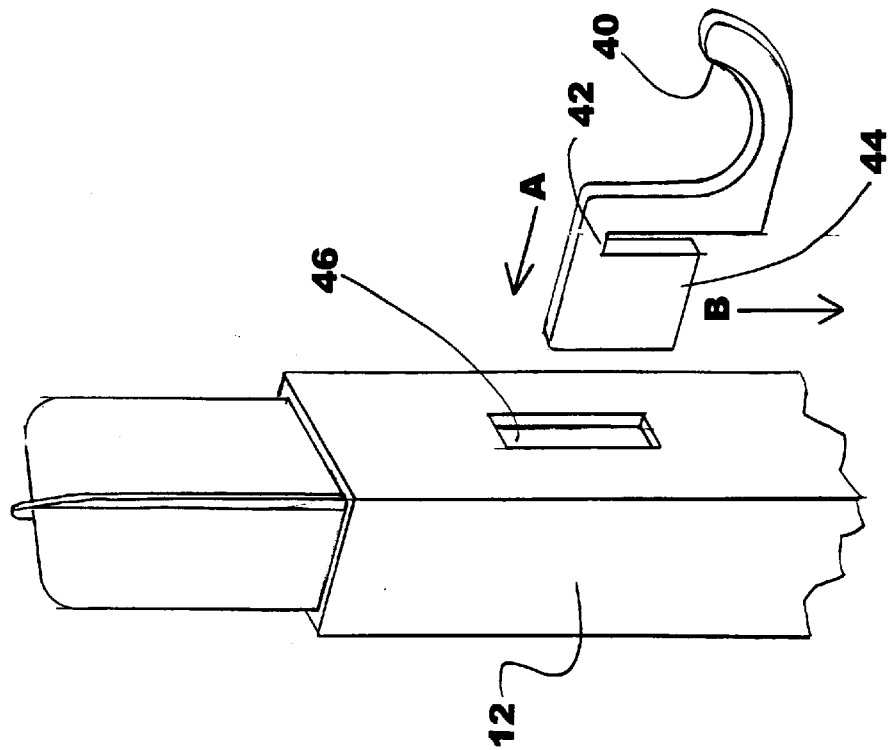
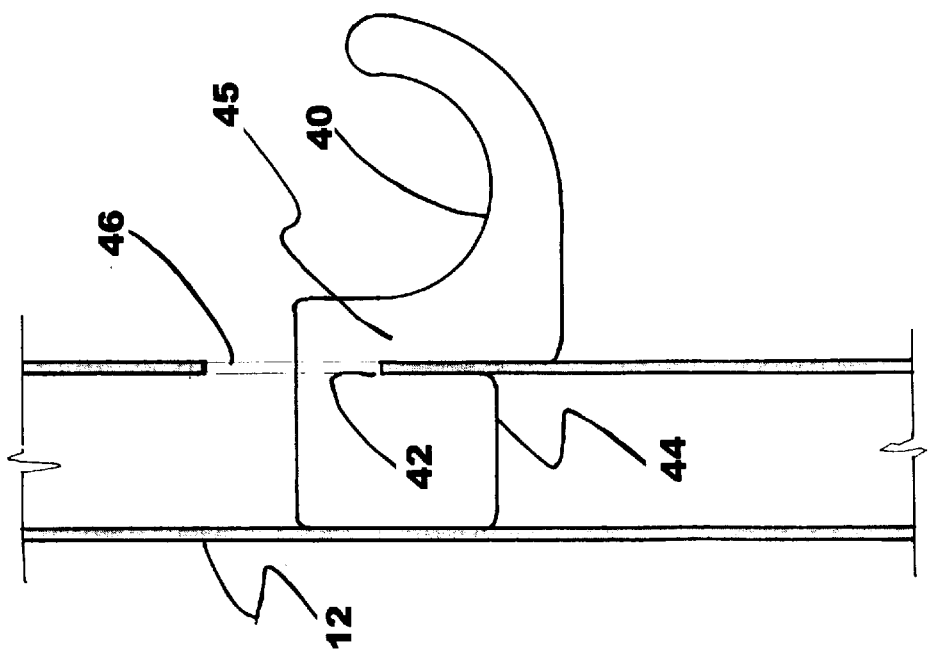

PORTABLE SECTIONAL POLE AND ATTACHING CONNECTORS

CROSS REFERENCES TO RELATED APPLICATIONS

Not applicable

STATEMENT REGARDING FEDERALLY-SPONSORED RESEARCH OR DEVELOPMENT

Not applicable

BACKGROUND OF THE INVENTION

This present invention relates to a portable sectional pole and its means of connection and, more particularly, to a portable sectional pole having one or more holding members adapted to support containers for administering substances into a user's body and for collecting substances eliminated from a user's body. The holding members are integral to the sectional pole and may be removable or concealable thereby further facilitating the portability of the pole. In addition, the sectional pole is self-supporting in that it is adapted to support itself or use any suitable, yet commonplace, external structure for support thereby enhancing its versatility.

Cost of medical has risen over the years and continues to rise. More and more emphasis is being placed on performing necessary treatment in a clinical setting or a hospital and then only releasing a patient after a patient's condition has reasonably stabilized. Post-hospitalization care in many cases is now performed by the patient or by third parties; be they family, friends, or paid professionals. Such post-hospitalization and post-treatment care may require intravenous feeding, intravenous administration of medications, and other forms of catheterization for introduction of substances into one's body (infusion therapy) or for the elimination of substances from one's body; such as, but not limited to, eliminations involved in perineal dialysis treatment.

Depending on the regimen involved, such administration can adversely affect one's lifestyle and dramatically inhibit one's quality of life. To administer to these needs, generally a device must be capable of holding and supporting a bag or suitable container. This bag or container either contains the substance to be administered to the user or is an empty receptacle for receiving expelled substances from the user. Many such devices currently exist in a variety of forms for use either the clinical setting or at home or other non-clinical setting. Some such devices are found in U.S. Pat. No. 4,511,157 issued to Wilt on Apr. 16, 1985; in U.S. Pat. No. 4,541,596 issued to Price on Sept. 17, 1985; in U.S. Pat. No. 4,744,536 issued to Bancalari on May 17, 1988; in U.S. Pat. No. 5,009,442 issued to Schneider on Apr. 23, 1991; in U.S. Pat. No. 5,135,191 issued to Schmuhl on Aug. 4, 1992; in U.S. Pat. No. 5,188,323 issued to David on Feb. 23, 1993; in U.S. Pat. No. 5,337,992 issued to Pryor on Aug. 16, 1994; and in U.S. Pat. No. 5,374,074 issued to Smith on Dec. 20, 1994. All these devices, alone or in combination, are well-suited for their intended purpose. Some, however, are extremely complex and difficult to use. Some require an additional component which itself is complex, such as a wheelchair or gurney for example, for proper use. Some are portable, some are collapsible, some are relatively easy to use. None, however, incorporates all the features necessary for relatively unobtrusive use and ease of use outside a clinical setting while simultaneously being portable, flexible, and multi-faceted as is the present invention.

Accordingly, several objects and advantages of my invention are to:

a. provide unique but simple and sturdy connectors to connect together sections of sectional poles to create poles of varying sizes;

b. provide a completely portable light-weight sectional pole which is easy to conceal, easy to transport, easy to assemble, and easy to use anywhere;

c. provide holding members on a portable pole which are capable of supporting a variety of containers for use and are concealable within or detachable from the portable pole when the portable pole is broken down;

d. provide for a variety of settings and locations on a support pole for holding containers necessary for tending to a user's health care needs;

e. provide a support pole which can adapt to and be supported by external objects having irregular configurations;

f. provide a support pole which, when attached to an external object, protects and does not damage the external object; and g. provide an inexpensive, fully functional, versatile, and relatively unobtrusive support pole for a user to administer to that user's health care needs in virtually any setting.

The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF SUMMARY OF THE INVENTION

The above-noted problems, among others, are overcome by the present invention. Briefly stated, the present invention contemplates a pole connector and a detachable sectional pole wherein the pole connector, at one end, is securely insertable into one end of a section of the pole, and another end of the connector has a set of at least three fins protruding from that pole section for removably attaching to a mouth of another pole section. The pole connector may be made of two to four or more segments.

The sectional pole has more than one section, each with a pole connector securely inserted into one end with the other end open and adapted to removably connect to a pole connector protruding from another pole section. The sectional pole has a support member adapted to attach to an external object, maintain approximate vertical stability, and protect the external object from damage while so attached. It also has one or more holding members which are concealable within the sectional pole or removable from the sectional pole and which are adapted to hold external objects thereon.

The foregoing has outlined the more pertinent and important features of the present invention in order that the detailed description of the invention that follows may be better understood so the present contributions to the art may be more fully appreciated. Additional features of the present invention will be described hereinafter which form the subject of the claims. It should be appreciated by those skilled in the art that the conception and the disclosed specific embodiment may be readily utilized as a basis for modifying or designing other structures and methods for carrying out the same purposes of the present invention. It also should be realized by those skilled in the art that such equivalent constructions and methods do not depart from the spirit and scope of the inventions as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIG. 4 is an exploded view of the connector to the portable section pole.

FIG. 5 is a cross-sectional plan view of a four segment pole connector fitted into a section of the portable sectional pole.

FIG. 6 is a detailed plan view of two segments of a four segment pole connector.

FIG. 7 is a perspective view of one embodiment of the support section of the portable sectional pole with attachable spacer and protector.

FIG. 11 is a partial sectional view of a removable holding member on the portable sectional pole.

FIG. 12 is a detailed exploded view of the removable holding member as illustrated in FIG. 11.

DETAILED DESCRIPTION OF THE INVENTION

Figure 1:
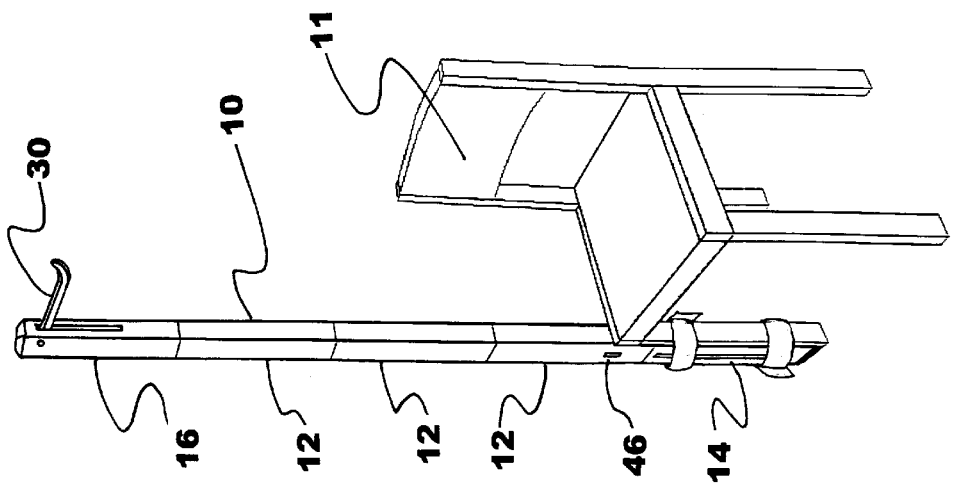
FIG. 1 is a perspective view of the portable sectional pole attached to a chair leg.

Referring now to the drawings in detail and in particular to FIG. 1, reference character 10 generally designates a portable sectional pole, with detachable sections 12, constructed in accordance with a preferred embodiment of the present invention. As illustrated here, the pole is attached to an external object; the leg of a chair 11. The vertical plane from the leg up is unobstructed. Attached to such an object, the pole 10 is secured and is approximately vertical (or perpendicular to the ground surface). As shown here, one section of the pole 10 is a support section 14 with flexible strap-like members connected to the support section 14 and wrapped around the leg of the chair 11.

Another section 16 at the top of the pole 10 shows an extending member 30 projecting therefrom which functions to hold objects thereon. As will be explained in detail below, this extending member 30 is retractable and concealable within the top section 16. A slot 46 is configured on a side of a section 12. This slot 46 may be on all sections 12 of the pole including the top section 16 and the support section 14 and any variations thereof. This slot 46 also may be on one or more sides of each of said sections. This gives the pole 10 greater versatility and flexibility of use. This slot 46 supports another extending member 40 (see FIG. 8) which is removable member which is adapted to hold objects thereon as needs dictate.

Figure 2:
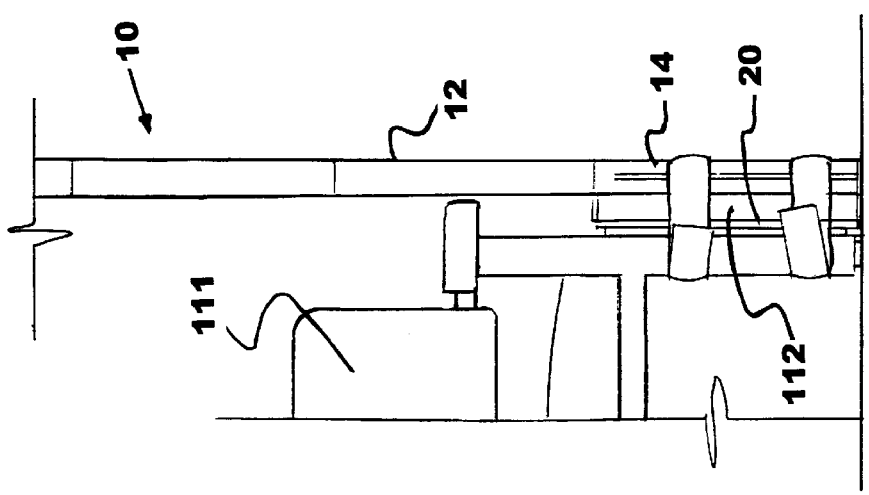
FIG. 2 a front elevation partial view of the portable sectional pole, with spacer and protector, attached to a chair leg.

FIG. 2 illustrates attachment of the pole 10 to an external object of irregular shape; a chair 111 having arms with arm rests which extend beyond a vertical plane of the chair's leg. The pole 10 is attached to a chair, or similar object of irregular shape, by utilizing a spacer 112 and/or a protector 20 inserted in between the support member 14 and the leg of the chair 111. The spacer 112 adds distance to the pole's vertical plane in relation to the vertical plane of the object to which attached such that each respective vertical plane is approximately parallel to one another after attachment and the pole 10 is approximately perpendicular to the ground surface. The protector 20 may have a cushion or pad thereon or be made, or consist, of a soft material on one or all sides such that, when it comes into contact with the leg of a chair, the soft material or cushion will serve as a barrier or cushion between the pole 10 and the leg of the chair and prevent damage to the leg of the chair or whatever external object is being used as support for the pole 10. The protector 20 and the spacer 112 are described in more detail below.

Figure 3:
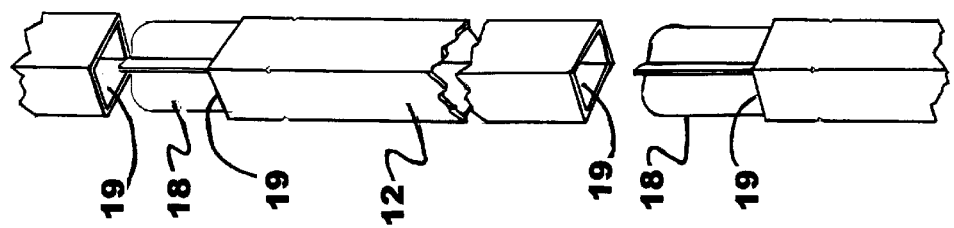
FIG. 3 is an exploded partial view of sections of the portable sectional pole and the connectors.

FIGS. 3 and 4 illustrate the pole connector 18 and connection of the pole sections 12 to one another (unless otherwise indicated, hereinafter this type of connection also includes connecting the top section 16 and the support section 14 and its secondary embodiment). The connector 18 is unique in that it provides greater structural integrity to the pole 10 after the sections 12 are connected to another than any other pole connectors previously seen or used for this purpose. Each pole section 12, 14, 16 has a mouth 19 at each end. A pole connector 18 is inserted into the mouth 19 of one end leaving the mouth at the other end open to receive and join with another section which contains the pole connector 18. As shown in these figures, the pole connector 18 has four fins, though three (or more) fins serve the same function particularly in those instances where the sections 12, 14, 16 are somewhat curvilinearly shaped. Four fins is best for poles having four or more sides.

The connector 18 generally may be made up of two to four segments or more. As illustrated in FIG. 4, the connector 18 is comprised of four segments with segments 81 and 82 being paired and segments 83 and 84 being paired. Each segment has a longitudinal slot 17 beginning at one end and terminating at approximately midpoint of the segment. After the four segments are paired, and with the two longitudinal slots as a guide, the two paired segments 81, 82 and 83, 84 are joined together forming the pole connector 18.

FIGS. 5 and 6 illustrate the detailed structure of the four segments. The ends 85 each segment are beveled and the outer surfaces (or exposed surfaces) of the pair segments are curvilinear. The function of the bevel is to seat the segments securely onto the inner surface of the section 12. The function of the curvature is to create a bias or force against the inner surface of the section. The angle of the bevel may range from about 1° to about 9°. For best results, the angle of the bevel should be about 2°. When the segments are paired, their outer or exposed surfaces are concave leaving a gap at the respective ends 85. The paired segments are joined at their respective slots 17 to thereby form a fin-like structure which inserts into the mouth 19 of any section 12. When two segments are used for the connector 18, no gap exists in the connector structure.

The pole connector 18 is also structured such that one end, referred to as an insert, has an external 'perimeter' substantially equal to the internal perimeter of the mouth 19 of a section 12 for securely mating with that section. Another end of the pole connector 18 is structured such that the other end has an external 'perimeter' approximately equal to the internal perimeter of the mouth 19 of a section 12 for removably mating with that section. In other words, the insert end of the pole connector 18 securely seats into the mouth 19 of a section 12, the other end projects from the mouth for removably mating with an open mouth 19 of another section 12.

Generally, the insert end should seat into the section 12 about two to about three inches, and the projecting end should project from the section about two to about three inches. This gives the pole 10 its ideal structural integrity. The insert end of the pole connector 18 also may be permanently affixed to a section. The insert end of the pole connector 18 may be a fin-like structure as above described or may be a solid structure.

FIG. 7 illustrates in detail the support member 14 shown in FIGS. 1 and 2. As shown in FIG. 7, one or more flexible straps 22 containing suitable fasteners, are connected to the support member 14. The fasteners on the flexible straps 22 may be any fastener suitable for the intended purpose including, but not limited to, hook-and-loop, snap tabs, and hook-and-eye. Hook-and-loop type fasteners are best and are illustrated. One element of the hook-and-loop is on one side of the strap 22 and the other element of the hook-and-loop is on the other side of the strap 22. To function as intended, it is not important which element is on which side. What is important is that cooperating fastening elements are on opposite sides of the strap 22 for as the strap 22 is wrapped around an external object, the opposite side communicates with the other side and fastens thereto.

On one side of the support member 14 are at least two apertures or receiving members 28 for registering and receiving a spacer member 112 or a protector member 20. A spacer member 112 is a member used to increase the base width of the support member 14 when the support member 14 alone, when attached to an external object, is not approximately vertical to the ground. It adds distance to the support member 14 so that it may stand approximately perpendicular to the ground surface as illustrated in FIG. 2. The spacer member 112 may come in varying widths to accommodate the varying gaps to be encountered in use. Like the support member 14, each spacer member 112 has at least two receiving members 28 on one side. Each spacer member 112 also has at least two connecting units 29 (not shown on spacer 112 but shown on protector member 20). The connecting units 29 may be a ball-like head having a shank which is connected to one side of the spacer member 112. The connecting units 29 are structured to register with the receiving member 28 on the support member 14 (apertures in this embodiment).

The protector member 20 also has connecting units 29 structured to register with the receiving member 28 of the spacer member 112 and, consequently, the receiving member 28 of the support member 14 in those situations where a spacer member 112 is not needed for vertical alignment. The protector member 20 may be made of a soft or cushion-like material or have a cushion or pad 21 on its outer surface.

The purpose of the protector member 20 is to prevent damage to the external objects as the pole 10 is attached and secured thereto. An end cap 13 may be placed over an exposed mouth of any section 12, 14, 16, and 112.

Figure 9:
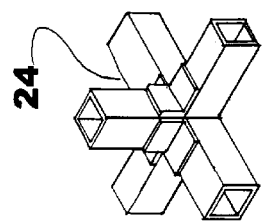
FIG. 9 is a detailed view of the second embodiment of the support section illustrated in FIG. 8.
Figure 8:
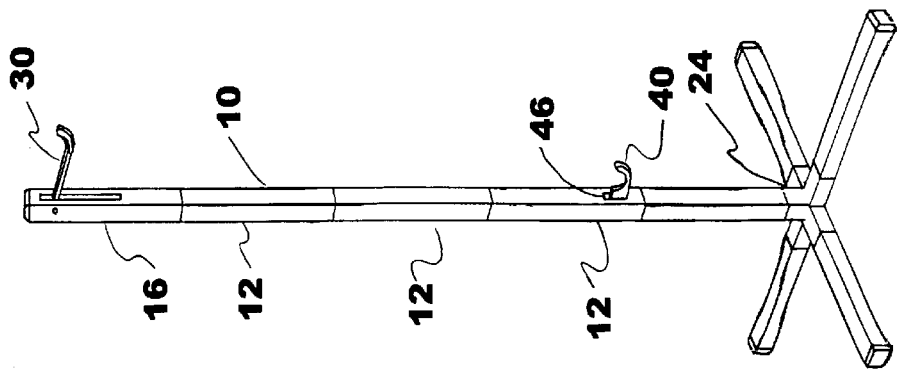
FIG. 8 is a perspective view of a second embodiment of the support section of the portable sectional pole.
Figure 13:
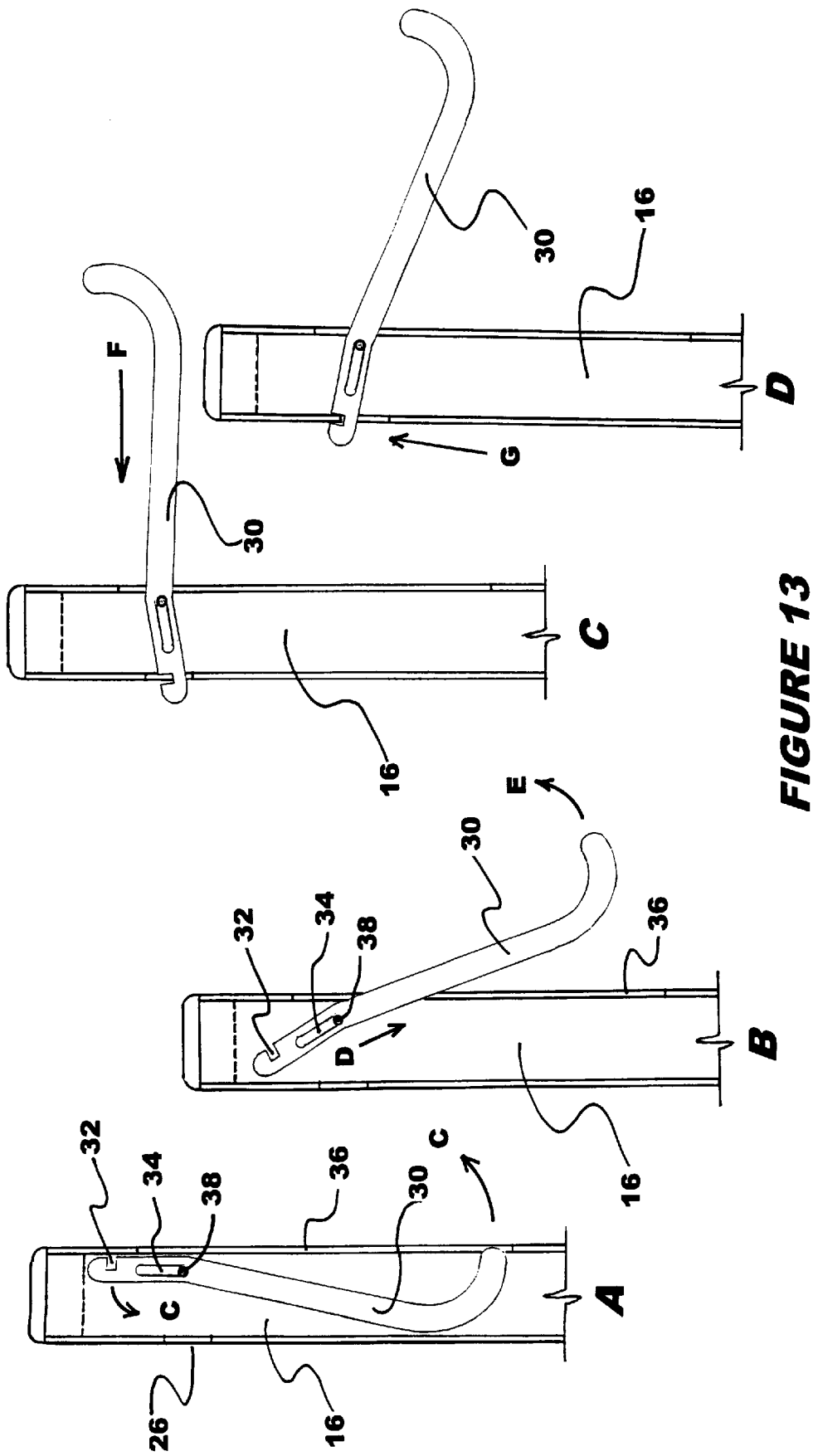
FIGS. 13A–13D are sectional views of the concealable retractable holding member shown in FIG. 10 illustrating its operation.

FIGS. 8 and 9 illustrate another embodiment of a support member 24 for the pole 10. This is a free-standing support member which has a approximately rigid base and does not require an external object. FIG. 9 illustrates this support member in detail. This support member 24 has a center with a mouth for receiving a section 12 therein. It has three or more approximately horizontal legs which extend outward. For greater portability, these horizontal legs may merely consist of short stubs each of which have mouths for receiving sections therein to provide support for the rigid base member 24 and the pole 10.

FIGS. 10–13 illustrate the holding members of this pole 10. Turning first to FIGS. 11 and 12, each section 12 may have one or more slots 46 therein. These slots 46 are structured to receive and retain a first extending member 40. The first extending member 40 is adapted to hold containers thereon as needed by a user. The first extending member 40 has a tab 44 to its rear, a leg 45 adjacent to the tab 44, and a slit 42 in between the tab 44 and the leg 45. The first extending member 40 connects to the pole 10 by insertion into the slot 46 tab-end first. The width of the tab 44 is approximately equal in dimension to the inner surface of the section 12 from the slot-side (slot 46) to its opposite wall. The width of the slit 42 is approximately equal in dimension to the thickness of the front wall of the section 12.

After insertion of the first extending member 40, in the direction of Arrow A, to approximately the rear of the inside surface of the section 12, the first extending member 40 is then moved downward in the direction of Arrow B until the slit 42 rests on the bottom of the slot 46 on the front side of that section 12. With the rear of the tab 42 adjacent to the rear inner wall surface of the section 12, the slit 42 securingly resting in the bottom of the slot 46, and the leg 45 adjacent to the front outer surface of the section 12, the first extending member 40 is securely, but removably, in place.

Figure 10:
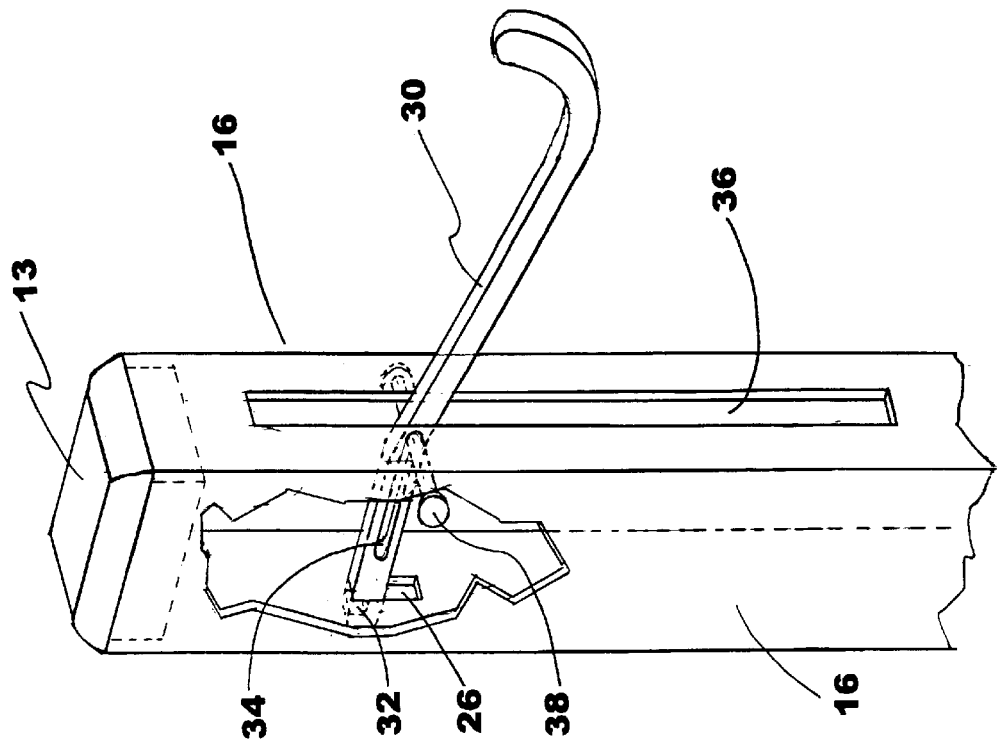
FIG. 10 is a cut-away view in perspective of a concealable retractable holding member contained within a section of the portable sectional pole.

FIG. 10 illustrates a second holding member which is retractable and concealable in the top section 16. The top section 16 has a second slot 36 on a side of the top section 16. A pin 38, approximately perpendicularly disposed in relation to the second slot 36, is connected to two opposing sides of the top section 16; these opposing sides are adjacent to the side bearing the second slot 36. On the top section 16, on a side opposite of the side which bears the second slot 16, is a third slot 26. A second extending arm 30 is held by the pin 38 and is pivotable into and out of the second slot 36, and is translatable into and out of the third slot 26 when extended.

Adjacent to the rear of the second extending arm 30 is a notch 32. Forward of the notch 32 is a channel 34. The channel 34 is the structure which holds the second extending arm 30 in the pin 38. The notch 32 seats into the third slot 26 and thereby maintains the second extending arm 30 in place and prevents it from translating forward, rearward, or downward. The operation of the second extending arm 30 is best illustrated in FIGS. 13A–13D.

In FIG. 13A, the second extending arm 30 is at rest and in place, concealed within the top section 16. To pivot the second extending arm 30 into its holding position it is first pivoted in the direction of Arrows C out of its resting place. Then, as shown in FIG. 13B, it is moved downward within the channel 34 in the direction of Arrow D, followed by an upward movement in the direction of Arrow E until it is approximately parallel with the ground surface. Its position at this stage is that illustrated in FIG. 13C. It is then moved rearward in the direction of Arrow F and toward the third slot 26. The pin 38 and the channel 34 cooperate and guide this movement. When the notch 32 is aligned with the third slot 26, the second extending arm 30 is moved in the direction of Arrow G. After the notch 32 seats into the top of the third slot 26, the second extending arm 30 has been set and is capable of bearing weight. After a user completes his health-care regimen, the second extending arm 30 is easily released and pivoted and concealed back into the cavity of the top section.

The present disclosure includes that contained in the present claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention. Accordingly, the scope of the invention should be determined not by the embodiments illustrated, but by the appended claims and their legal equivalents.

The invention claimed is:

1. A pole connector for detachable sectional poles of the type having pole sections with each said pole section having at least two ends and a mouth at each of said at least two ends, each mouth further having an internal perimeter thereat, said pole connector comprising:
   a. a first set of at least three fins having an external perimeter on one end which is adapted to be approximately equal to the internal perimeter of the mouth of one pole section into which said first set of at least three fins is removably attachable, said fins having an outer edge adjacent to said external perimeters, said outer edge being compressibly split; and
   b. an insert member having an external perimeter on the other end of said at least three fins which is adapted to be substantially equal to the internal perimeter of the mouth of another pole section into which said insert member is securably attachable;
whereby when one said pole section is inserted into the first set of at least three fins of said pole connector, the outer edges of said at least three fins compress thereby exerting outward pressure on the pole section and thereby holding the pole section more firmly onto said pole connector.

2. The pole connector as defined in claim 1 wherein said insert member comprises a second set of at least three fins.

3. The pole connector as defined in claim 2 wherein said second set of at least three fins further have an outer edge adjacent to its perimeter, said outer edge being compressibly split.

4. A portable sectionally detachable pole comprising:
   a. a plurality of sections, each of said plurality of sections having a first end and a second end and further having a mouth at each said end; and
   b. connector means for connecting any one of said plurality of sections to any other one of said plurality of sections; said connector means comprising a first set of at least three fins having an external perimeter approximately equal to an internal perimeter of a mouth of one section, said first set of at least three fins removably attachable to said mouth of said one section, said fins having an outer edge adjacent to said external perimeters, said outer edge being compressibly split, and an insert member having an external perimeter substantially equal to an internal perimeter of a mouth of another section, said insert member connected to said first set of at least three fins and securably attachable to said mouth of said another section whereby when one said section is inserted into the first set of at least three fins of said pole connector, the outer edges of said at least three fins compress thereby exerting outward pressure on the section and thereby holding the section more firmly onto said pole connector.

5. The pole as defined in claim 4 further comprising a support means for supporting said pole, said support means located on any one of said plurality of sections.

6. The pole as defined in claim 5 wherein said support means comprises at least one flexible member adapted to securingly engage an external structure and thereby support said pole.

7. The pole as defined in claim 5 wherein said support means comprises a strap-like member having a first side and a second side and further having cooperating fastening means on each of said sides for securingly engaging said first side to said second side.

8. The pole as defined in claim 7 wherein said fastening means comprises hook-and-loop fasteners.

9. The pole as defined in claim 5 wherein said support means comprises a rigid base member attachable to any one of said plurality of sections, said rigid base member having a center and plurality of horizontal legs extending from said center.

10. The pole as defined in claim 5 further comprising a spacer member insertable adjacent to said support means for establishing an approximately vertical alignment of said pole.

11. The pole as defined in claim 5 further comprising a protector member insertable adjacent to said support means for establishing a protective barrier between said support means and an external object to which said pole is attached.

12. The pole as defined in claim 4 further comprising a holding means for holding objects thereon, said holding means connectable to any one of said plurality of sections.

13. The pole as defined in claim 12 wherein said holding means comprises a first slot in said one of said plurality of sections and an extending member in said one of said plurality of sections whereby said first extending member is detachably securable in said first slot of said one of said plurality of sections.

14. The pole as defined in claim 4 further comprising a second holding means for holding objects thereon, said second holding means connected to any one of said plurality of sections.

15. The pole as defined in claim 14 wherein said second holding means comprises a second slot in said one of said plurality of sections and a second extending member in said one of said plurality of sections whereby said second extending member is pivotable in and out of said one of said plurality of sections and is securely retainable in said second slot.

16. The pole as defined in claim 4 wherein said second set of at least three fins further have an outer edge adjacent to its perimeter, said outer edge being compressibly split.

* * * * *